United States Patent [19]

Johnson

[11] 4,228,353
[45] Oct. 14, 1980

[54] MULTIPLE-PHASE FLOWMETER AND MATERIALS ANALYSIS APPARATUS AND METHOD

[76] Inventor: Steven A. Johnson, 136 N. First West, Preston, Id. 83772

[21] Appl. No.: 902,208

[22] Filed: May 2, 1978

[51] Int. Cl.$^3$ .................. G01F 1/00; G01N 21/00; G01N 23/20; G21K 1/00
[52] U.S. Cl. .................. 250/356; 250/277 R; 250/445 T; 73/861.04; 73/861.06
[58] Field of Search ............... 250/356, 277 R, 445 T; 73/194 R, 194 E, 194 M, 194 A

[56] References Cited

U.S. PATENT DOCUMENTS

| Re. 28,686 | 1/1976 | Coulthard | 73/194 E |
|---|---|---|---|
| 3,927,318 | 12/1975 | Macouski | 250/445 T |
| 3,980,882 | 9/1976 | Garfield et al. | 250/277 R |
| 4,053,779 | 10/1977 | Barbieri | 250/445 T |
| 4,057,725 | 11/1977 | Wagner | 250/445 T |
| 4,125,769 | 11/1978 | Marten et al. | 250/277 R |

FOREIGN PATENT DOCUMENTS 2304618  8/1973  Fed. Rep. of Germany ........... 250/356

OTHER PUBLICATIONS

Flemons, R. S., "A New Non-Intrusive Flowmeter," National Bureau of Standards Special Publication 484, Proceedings of the Symposium on Flow in Open Channels and Closed Conduits Held at NBS Gaithersburg, Md., Feb. 23-25, 1977 (issued Oct. 1977).

*Primary Examiner*—Alfred E. Smith
*Assistant Examiner*—T. N. Grigsby
*Attorney, Agent, or Firm*—J. Winslow Young; H. Ross Workman; Rick D. Nydegger

[57] ABSTRACT

An apparatus and method for elemental analysis and non-invasive measurement of the mass flow rate and/or density distribution of a multiple-phase system. The apparatus includes at least two X-ray sources, transmission detectors for the X-ray sources, fluorescence detectors, and collimators all of which are suitably indexed and multiplexed to provide information corresponding to the density distribution, elemental composition, phase composition, and/or flow rate of the system. Energy selective detectors are included in the apparatus to provide selective fluorescent radiation detection for fluorescence emitted by elements excited by the X-rays as a technique for obtaining an indication of the elemental composition of the system. X-ray sources and transmitted X-ray detectors are used to detect the density of the multiple-phase system at each point in a cross-section of the system. Corresponding second X-ray sources and detectors are mounted a moderately short distance from the first X-ray source and detector combination. The total mass flow rate and density distribution of the system is the integral over the area of the conduit for a plurality of point mass transfer rates and densities. A conventional computer system is included as part of the flowmeter and materials analysis apparatus to correlate and process the readings obtained by the various detectors and obtain thereby the mass flow rate, density and elemental composition of the multiple-phase system.

19 Claims, 10 Drawing Figures

MULTIPLE-PHASE FLOWMETER AND MATERIALS ANALYSIS APPARATUS AND METHOD

BACKGROUND

1. Field of the Invention

This invention relates to multiple-phase density flowmeters and materials analysis apparatus and, more particularly, to an x-ray multiple-phase flowmeter, density and fluorescent materials analysis apparatus and method.

2. The Prior Art

Historically, the measurment of the flow of fluids (both gases and liquids) may be categorized as encompassing (1) invasive measurement techniques and (2) non-invasive techniques. Invasive techniques utilize devices extending into the flow of the fluid and include probes, the introduction of markers, orifices and the like.

Non-invasive techniques externally measure a particular flow-dependent property such as changes in the optical, acoustic or electromagnetic properties of the fluid. Unfortunately, these latter techniques generally require a nearly transparent fluid and are not readily adaptable to a two phase or multiple-phase system. Multiple-phase systems are those for example, found in gas and fluid mixtures, steam-water systems or solid-fluid systems such as a slurry pipeline wherein coal particles are transported by being entrained in a gas or water stream.

Currently, the measurement of mass flow rates, fluid velocity and density in steam-water mixtures in boilers, nuclear reactors, and associated piping is difficult and, unfortunately, error prone. This is particularly true using the current invasive or non-invasive techniques. Present non-invasive techniques are not sufficiently refined to provide the desired accuracy particularly at each point in a cross section of a pipe or a vessel. However, increased demand for steam-driven turbine systems for electrical generators using nuclear fuel coupled with an increasing concern for nuclear safety has created a demand for increasingly accurate flow measurement for safety monitoring devices. Accurate flow measurement devices are also specified for conventional process instrumentation but, more especially for instrumentation for special purpose nuclear reactors and associated equipment designed to evaluate safety features and responses in the event of an accident, particularly a loss of coolant accident in a pressurized water nuclear reactor.

Increased emphasis is also being directed toward the use of coal-fired generating systems. It is, therefore, becoming increasingly important to be able to transport coal over long distances, up to several hundred miles, from the coal deposits to the power generating station. Currently one of the most economical techniques is the slurry pipeline system. Accordingly, it is also important to be able to accurately measure the mass flow rate of the coal particles in the slurry pipeline. The use of invasive techniques in slurry systems, is practically useless because of the difficulties created by the particles of coal in the fluid stream. For example, probes become clogged and restriction orifices create areas of sedimentation thereby destroying the utility of an invasive technique for measuring such a two phase system.

Other applications could also advantageouly utilize a mass flow rate measurement system wherein a multiple-phase system is being measured. Measurement of mass flow rates should also lend itself to density and/or concentration measurements. This could be useful in reactors, both chemical and nuclear, as well as certain process streams.

Accordingly, it would be a significant advancement in the art to provide a mass flow rate meter apparatus particularly one using a non-invasive measurement technique. Another advancement in the art would be to provide an apparatus and method whereby an essentially single-phase system may be accurately measured by the controlled injection of a second phase into the system and thereafter non-invasively measuring the two phase system. It would also be an advancement in the art to provide an apparatus and method for measuring density and phase concentrations in a multiple-phase system. Another advancement in the art would be to provide an apparatus and method for analyzing chemical elements by non-invasive, x-ray fluorescent techniques. It would also be an advancement in the art to provide an apparatus to reconstruct the cross sectional flow and density distribution of phase components in a flow system. Such an apparatus and method is disclosed and claimed herein.

BRIEF SUMMARY AND OBJECTS OF THE INVENTION

The present invention relates to an apparatus and method for measuring the mass flow rate, density distribution and elemental composition of a multiple phase system. Cross correlation of measurements provides useful information relative to reactions in reaction chambers, density distributions, elemental composition, flow patterns, and flow rates. The basic concept of this invention is to measure the density distribution of the multiple phase system at each point in a given cross section of a system and, correspondingly, the velocity of the multiple phase system at each point in the same cross section. The mass flow rate of the multiple-phase system at each point in a cross section is a product of the density and the normal or longitudinal velocity of the multiple-phase system at that point. The total mass flow rate of the multiple-phase system through a conduit is obtained as the integral of the point mass transfer rate over the area of the conduit. The density of the multiple-phase system at each point in the conduit cross section can also be obtained using well-known, cross-sectional reconstruction techniques. The velocity at each point in a cross section consists of normal and transverse components, both of which may be determined by cross correlation techniques. A two phase system can be created in a one phase system or the measurability of the components in an existing two phase system enhanced by injecting a known quantity of a known phase into the system and using the mass flowmeter apparatus and method of this invention to obtain the mass flow rate of the overall system. This known phase may also be one of the other phases.

It is, therefore, a primary object of this invention to provide improvements in the measurements of the mass flow rate of a two phase system.

Another object of this invention is to provide improvements in mass flowmeters.

Another object of this invention is to provide improvements in the method of measuring the longitudinal and transverse components of the mass flow of the multiple density system.

Another object of this invention is to provide an improved method for measuring the mass flow rate of a single phase system.

Another object of this invention is to provide an improved apparatus for measuring the mass flow rate of a single phase system.

Another object of this invention is to provide an apparatus for detecting the elemental composition of a system.

Another object of this invention is to provide an apparatus for detecting the density distribution of a system.

Another object of this invention is to provide a method for measuring flow and obtaining materials analysis at each point in a cross section as well as providing for the measurement of total flow rate and materials analysis.

These and other objects and features of the present invention will become more fully apparent from the following description and appended claims taken in conjunction with the accompanying drawing.

DETAILED DESCRIPTION OF THE PREFERRED EMBODIMENTS

The invention is best understood by reference to the drawing wherein like parts are designated with like numerals throughout.

General Discussion

As used throughout, the term "radiation" also includes radiation of the electromagnetic spectrum suitable in the practice of this invention, including, but not limited to gamma x-ray visible light, ultraviolet, and infrared radiation. Ultrasound radiation could also be suitable in the practice of this invention in certain circumstances. Importantly, the use of suitable radiation permits the non-invasive measurement of properties inside a system by providing the ability to penetrate the system and the containment apparatus for the system while being detectable as a function of the characteristics of the system penetrated.

One primary objective of this invention is to measure the mass flow rate (kilograms/second) of a particulate matter (solid) such as coal entrained in a fluid phase in a pipeline by a non-intrusive x-ray method. A secondary objective of this invention is to simultaneously determine the average density (grams/cubic centimeter) and the average transport velocity (meters/second) of the particulate flow. Another secondary objective of this invention is to provide a determination of the density stratification and flow velocity profiles expressed as first and second statistical moments (i.e., to find the cross-sectional, two dimensional, spatial variation of the time mean and time standard deviation of these transport parameters). Another ojective of this invention is to reconstruct the fluid velocity profiles and measure the mass flow rates of multiple-phase fluid flows by use of ultrasound cross correlation transmission techniques.

The basic concept is to measure both the density and the velocity of the particulate matter or mixed fluid phases at each point in the same cross section. In the remainder of this patent application, the term particulate matter shall be used interchangeably with the terms second phase and gas bubbles without changing the operation of the invention. The mass flow rate of the particulate matter at each point in the cross section is the product of the density and velocity. The use of cross-correlation for obtaining velocity information is well established in certain fields.

The total particulate mass flow rate is the integral of the point mass transfer rate over the area of the conduit. The density of the particulate matter at each point in the conduit's cross section can also be obtained from well-known cross-sectional, x-ray reconstruction techniques using projections. For example, see Scientific American, October 1975, "Image Reconstruction from Projections", pages 56–68 for an article co-authored by myself which explains this technique. The velocity of the particulate matter in the conduit at each point in the conduit's cross section may be obtained by cross-correlating two sets of density reconstructions made in each of two separate conduit cross sections, separated by a moderately short distance.

In many practical applications of the mass flowmeter of this invention it may be possible to eliminate the requirement for reconstructing the density of the two phase system at each point in the conduit cross section. This can be done by using information from only one projection in each of two separated sections. This approach would result in major savings in costs since it would not be necessary to rotate the x-ray source or to compute the reconstructed density values. To accomplish the foregoing, cross-correlations are performed with a projection (or line integral) of density along a pair of paths from a corresponding pair of x-ray sources to two detector arrays. The total particulate mass flow rate is computed as above. The cross-correlation signal level may be improved, if necessary, by introducing increased correlation in the flow by using supplementary pules of a second phase injected into the system such as air and the like.

Mathematical Analysis

In derivation of all calculations in the simplified theory (Method 1), an implicit assumption is made that the particulate matter moves at the same velocity at corresponding points along each set of the two parallel x-ray projection paths corresponding to the two sources, respectively. This assumption is relaxed in the more complete theory which is presented later in Case 2 of Method 2.

Figures 4, 5:
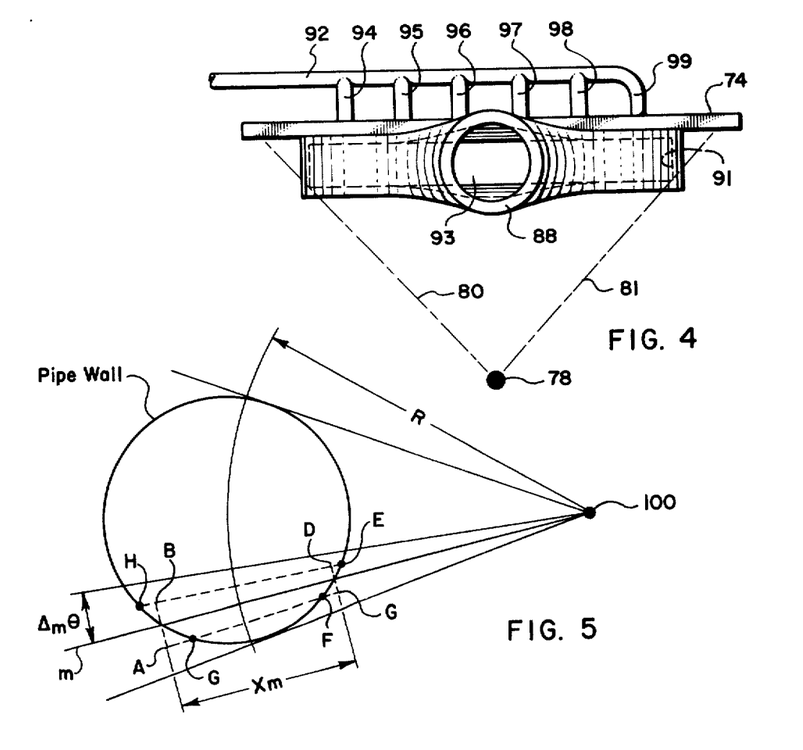
FIG. 4 is an end view of the mass flowmeter of FIG. 3.
FIG. 5 is a schematic illustration of the theoretical basis for the mathematical derivations used in the method of this invention.
Figure 6:
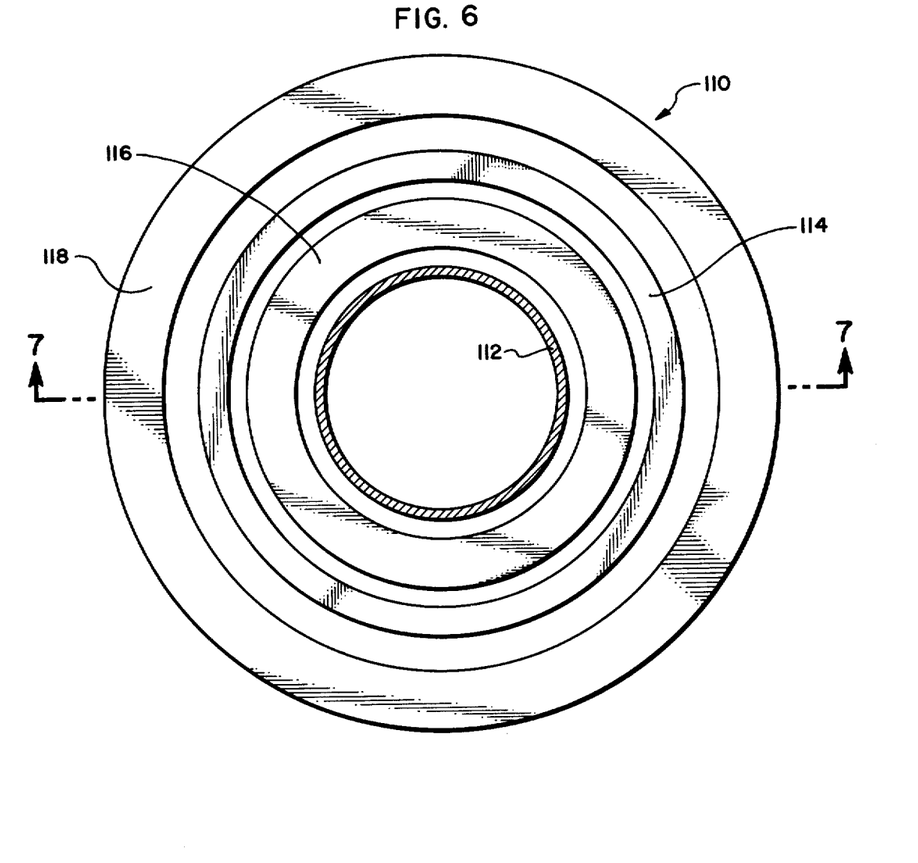
FIG. 6 is a plan view of a third preferred embodiment of the apparatus of this invention.

A more detailed technical description of the mass flow measuring technique is now given. Referring to FIG. 5 it is seen that the x-ray intensity, I(m), along a typical ray, ray m, is given by $$I(m) = M^*(M) \exp(-\int \mu(x)dx) \qquad (1)$$

where $I^*(m)$ is the measured x-ray intensity with the pipe empty.

Let $\mu(x)$ be the total linear attenuation coefficient given by $$\mu(x) = \mu_1\epsilon_1 + \mu_2\epsilon_2 + \mu_3\epsilon_3 + \ldots + \mu_i\epsilon_i(x) + \ldots \mu_n\epsilon_n \qquad (2)$$

where $\mu_i$ is the linear attenuation coefficient of the $i^{th}$ phase or material or element and $\epsilon_i(x)$ is the volume fractional concentration at point x of phase or material i. Note that $\epsilon_1(x) + \epsilon_2(x) + \ldots \epsilon_n(x) = 1$ since the sum of all fractional parts must equal the whole. It is also clear that $\mu_i\epsilon_i$ can be written as $$\left(\frac{\mu_i}{\rho_i}\right)(\epsilon_i\rho_i) = \mu_{mi}\rho_{mi} \text{ where } \mu_{mi} = \left(\frac{\mu_i}{\rho_i}\right)$$

is the mass linear attenuation coefficient, $\omega i$ is the fractional density of material of phase i, and $\rho i$ is the density of pure material of phase i. When Equation (2) is substituted into Equation (1) it is seen that the measure intensity I(m) is a function of many materials along the path.

A method for reconstructing the three-dimentional concentration of many materials from Equation (1) applied to many paths has been given in a paper by Berggren, Johnson et al (Berggren, M. J., S. A. Johnson, J. F. Greenleaf, R. A. Robb, R. E. Sturm, G. T. Herman, and E. H. Wood: "A Method for Selective Tissue and Chemical Element Three-Dimensional Reconstructive Imaging from Radiographic Film and Roentgen-Video Images", Image Processing for 2-D and 3-D Reconstruction from Projections: Theory and Practice in Medicine and the Physical Sciences. A Digest of Technical Papers, August 4-7, 1975, Stanford, California, pp. MB2-1 to MB2-4, Optical Society of America). This method depends upon making each measurement along many paths using many different incident spectral energy distributions. It is clear that this method or any method which produces information about only one element in a projection may be used with the theory combining reconstruction and cross correlation which will be subsequently derived. It is also clear that any detector which integrates the selective fluorescence radiation emitted by elements along a line path also can produce a material selective projection similar to Equation (1) and can be used with the cross-correlation and reconstruction method herein described to measure mass flow velocity cross sections of specific materials.

The case where insufficient information is provided to determine all the $\mu_i$ in Equation (2) is of particular interest. Suppose Equation (2) has been reduced to only two terms $$\mu(x) = \mu_i \epsilon_i(x) + \mu_2\epsilon_2(x) \qquad (3)$$

alternately, Equation (3) may be thought of as only two phases present. Note, $\epsilon_1 = 1 - \epsilon_2$ then upon substitution into equation (1) we obtain $$I(m)/I^*(m) = \exp[-\mu_1 \int dx]\exp[-(\mu_1 - \mu_2) \int \epsilon_2(x)dx] \qquad (4)$$

which may be rewritten as $$\{\ln[I(m)/I^*(m)] + \mu_1 \int dx\}/(\mu_2 - \mu_1) = \int \epsilon_2(x)dx \qquad (5)$$

Define $D_2(m)$ to be the mean density of phase 2 along ray m given by $$D_2(m) = \rho_2 \int_m \epsilon_2(x)dx / \int_m dx \qquad (6)$$

It is clear than D(m) can be written in terms of measured or known quantities I(m), $I^*(m)$, etc., by substituting $\int \epsilon_2(x) dx$ from Equation (6) into Equation (5). It is also clear that the density of phase 1 could also be measured in a similar manner using a similar derivation.

By elementary steps it is seen that $D_1(m)$ can be defined also in terms of the transmitted intensity with the pipe filled with 100% material 1. Let $I_1(m)$ be the transmitted intensity for the case of 100% material 1 (i.e., phase 1) in the pipe then:

$$D_2(m) = \rho_2 \ln[I(m)]/[(\mu_2 - \mu_1) \int dx] \qquad (7)$$

In the subsequent derivations the subscripts 1 and 2 will be dropped from D and the material described will be defined by context.

This last expression is used to compute the average density from intensity measurements and geometry of ray m. More specifically, the measurement on path ma may be defined by D(m,a) and the corresponding measurement on path m(b) by D(m,b).

The velocity of the second phase material such as a coal particles is found by cross-correlation techniques as follows. Define the time variable density D(m) from detectors a and b by D(m,a,t) and D(m,b,t) respectively. The cross-correlation function f (a,b,m,$\tau$) is defined by $$Z(m,a,b) = F(a,b,m,\tau) \qquad (8)$$
$$= \int_{-\infty}^{\infty} D(m,a,t)D(m,b,t + \tau)dt$$

In practice, the limits of the integral are usually replaced by finite values, large enough to allow accuracy, but small enough to facilitate computational speed. The function f (a, b, m, $\tau$) reaches a maximum at a time $\tau$ corresponding to the average time for a coal particle to travel from x-ray fan beams 80–81 or to a fan beams 82–83 or b. Let this time be given by the inverse function $F^{-1}$ given by $$F^{-1}(M_{ax}Z_{mab}) = \tau(m;a,b) \qquad (9)$$

Alternately, $\tau$ could be defined as the center of gravity of f(m, a, b, $\tau$) with respect to $\tau$.

The average velocity of travel of material fluxuations along the plane define by the straight lines from source 1 along ray m(1,a) to detector a and from source 2 along ray m(2,b) to detector b in the pipe to be V(m,a,b) given by $$V(m,a,b) = L(a,b)/\tau(m;a,b) \tag{10}$$

In general, rays m(1, a) and m(2, b) need not be parallel to each other. The velocity, V(m,a,b), would then contain angular and radial components as well as a longitudinal component. For many applications, Method 1, described hereafter, may be used and then only the longitudinal component is required and, therefore, rays m(1,a) and m(2,b) are chosen mutually parallel for each choice of point a.

Simultaneous sets of Equations (10) and (7) now allow the coal mass flow to be computed by a variety of methods. Two methods will be given for illustration. The first method (Method 1) is approximate but simple. The second method (Method 2) has potentially greater accuracy but requires more complexity in data acquisition and processing.

Method 1 uses only one projection data set and sums the mass flow in many fan-like sectors. Let R be the distance from the source 100 (FIG. 5) to the center of the pipe and $\Delta(\theta,m)$ be the mth increment of angle $\theta$. Let L(a,b) be distance between the two x-ray source planes. Referring to FIG. 5 it is seen that the area of a sector is $(x(m)R \Delta (\theta,m)$. Note X(m) is $X_m$ and $\Delta (\theta,m)$ is $\Delta_m \theta$ respectively in FIG. 5. Using the relationship that mass flow is the integral of the product of density and velocity over the cross-sectional area of the pipe, it can be shown that the mass flow rate, (dM/dt), is given approximately by a summation over sectors corresponding to each path m.

$$dM/dt = \frac{\sum_m [(D(m,a) + D(m,b)]x(m)RL(a,b)\Delta(\theta,m)}{2\tau(m,a,b)} \tag{11}$$

A modification to Method 1 would use the Abel inverse Abel transform pairs with the assumption of circular symmetry, to reconstruct the two dimensional velocity function V*(x,y), and the two dimensional density functions D*(a;x,y) and D*(b;x,y) everywhere in the cross section of the pipe. Here x,y refers to the two dimensional coordinates in the cross section. Then, the integration would be more exact and could be written as $$dM/dt = \left(\frac{1}{2}\right) \int\int D^*(a;x,y) + D^*(b;x,y)V^*(x,y)dxdy \tag{12}$$

It is predicted that either of the expressions D*(a;x,y) or D*(b;x,y) may be substituted for [D*(a;x,y)+D*(b;x,y)]/2 with little loss in accuracy in Equations (11) and (12). This modification using Abel transforms would be appropriate for coal density distributed in circular symmetry in circular symmetric flows.

Method 2 uses many source positions in each plane to obtain projection data from which the actual density $\rho(x,y)$ and flow velocity V*(x,y) at each point in the pipe may be computed. The total mass flow is then given by appropriate versions of the general equation.

$$dM(t)/dt = \int\int \rho(x,y,t)V^*(x,y,t)dxdy \tag{13}$$

The computation of the functions $\rho(x,y)$ and V*(x,y) may be done in a variety of ways some of which will be listed.

Case 1

If the multiple x-ray source pulsing sequence for each plane is more rapid than the average movement of a particle across the x-ray beam in each plane then $\rho(x,y,t)$ may be considered to be an instantaneous cross sectional density. In this case $\rho(x,y,t)$ may be computed in a straight forward manner by the ART, convolutional or other reconstruction techniques. The function V*(x,y,t) may be computed by cross correlation techniques from the $\rho(x,y,t)$. If the flow has no components perpendicular to the axis of the pipe, then the longitudinal flow velocity associated with each differential area dxdy is computed by cross correlating only between the corresponding points in both planes. Let $\rho_a(x,y,t)$ and $\rho_b(x,y,t)$ be the computed densities in planes a and b, respectively. Then the average velocity is $$V^*(x,y,t) = L(1,2)/F_{ii}^{-1}[\max t \int \rho_a(x,y,\tau - t)\rho_b(x,y,\tau - t - t_1)d\tau] \tag{14}$$

The equation is similar to Equations (9) and (10) and states that velocity is the length divided by the average transit time.

If the flow has components normal to the axis of the pipe then the flow stream lines will not necessarily thread each cross section at the same corresponding position.

The intersection of a stream line originating in the first cross section with a second cross sections may be found by cross correlating the density at the point in the first cross section with all points in the second cross section. We shall assume that the stream line crosses the second cross section at the point of the greatest cross correlation value. Thus by heuristic arguments one would write the total mass flow as the weighted produced of the density along a flow line and the corresponding velocity summer over all pairs of differential surface areas in the two cross sections. The velocity would be found from the peak of each cross correlation pairs and the weight would be proportional to the height or strength of the cross correlation peak.

$$dM(t)/dt = \sum_a \sum_b W_{\alpha\beta}\rho_a(x_\alpha,y_\alpha,t)V_{\alpha\beta}(x_\alpha,y_\alpha,x_\beta,y_\beta)\Delta A_a \Delta A_b \tag{15}$$

Here $W_{\alpha\beta}$ is the weight for path $(\alpha,\beta)$ from point $\alpha$ in plane a to point $\beta$ in plane b, $\rho_a(x_{60}, y_\alpha, t)$ is the starting density, in plane a at point $\alpha$, $V_{\alpha\beta}$ is the velocity along path $(\alpha,\beta)$ and $\Delta A_a$ and $\Delta A_b$ are the corresponding differential areas in cross sections a and b respectively.

Case 2

If the ratio of x-ray source pulsing speed to flow speed is not sufficiently large, then the method of case 1 is not applicable and some other technique must be employed. Techniques based upon cross correlation of projection data rather than reconstruction picture elements (pixels) would not necessarily be affected by pulsing speed. Method 1 would serve as such an example for only one projection direction, but what is proposed here is a more accurate version which would use cross correlated data from all projection directions. This proposed method would retain the feature of performing cross correlation operations on projection data which is the attracitve feature of Method 1, yet would permit reconstruction of cross sectional flow. In brief, this method would allow slowly changing flows to be reconstructed by analysis of the time cross correlation function between all permutations of detector pairs (A,B) where A is in plane a and B is in plane b. This method will be shown to be an extension of Case 1 by use of a simple mathematical argument.

The derivation of the method suitable for Case 2 starts with the observation that the method of Case 1 may be written in terms of a series of linear operators. The total mass flow rate is given by Equation (15) and the velocity factor is given by Equation (14). The cross correlation operation on the two reconstructed time-variable density functions $\rho_a$ and $\rho_b$ is of particular importance. This operation may be written symbolically using the symbol to indicate cross correlation so that:

$$(\rho_a \quad \rho_b)_\tau = \int \rho_a(x_\alpha, Y_\alpha, t)\rho_b(x_\beta, Y_\beta, t-\tau)dt \quad (16)$$

However, $\rho_a$ and $\rho_b$ each are related to the projection data by a reconstruction operator such as $F_{Rcaa A}$ through the relationship:

$$\rho_a(x_\alpha Y_{\alpha,t}) = \rho_{a\alpha} = F_{Rcaa A}D_{aA}$$

$$\rho_b(x_\beta, Y_\beta, t) = \rho_{b\beta} = F_{Rcb\beta B}D_{b\beta} \quad (17)$$

Where $D_{aA}$ and $D_{bB}$ are the set of projection data at detectors A and B from planes a and b, respectively. Thus Equations (16) and (17) may be combined as follows:

$$(\rho_{a\alpha} \quad \rho_{b\beta}) = \int F_{RCaaA}D_{aa}(t)F_{RCb\beta B}D_{b\beta}(t-\tau)dt \quad (18)$$
$$= \int F_{RCaaA}F_{RCb\beta B}\int D_{aa}(t)D_{b B}(t-\tau)dt$$
$$= \int F_{RCaaA}F_{RCb\beta B}(D_{a\beta} \quad D_{b\beta})_\tau$$

Equation (18) states that the cross correlation between pixel $\alpha$ in plane a and pixel $\beta$ in plane b can be found by: first, cross correlating all projection pairs (A,B) where A is from plane a and B is from plane b, then next operating with $F_{Rcb\beta B}$, and finally operating with $F_{RcaaA}$.

In the foregoing discussion no specific form for the reconstruction operator was given. For this invention some type of ART or convolution fan beam or equivelently effective algorithm is necessary. These algorithms are well known. For illustrative purposes an explicit form of the convolution reconstruction operator will be given for parallel x-ray beam illumination. (The operator is simpler for the parallel beam case). A similar explicit form is known for the convolution fan beam algorithm or ART algorithm. For the parallel beam case $F_{RcaaA}$ is a convolution operation over detector variable $r'$ followed by a summation over the sources j. Thus $$\rho_{aa}(\chi_\alpha, Y_\alpha, t) = \quad (19)$$
$$\sum_j D^*_{aa}(\chi_\alpha, \cos\phi_j + Y_\alpha, \sin\phi_j, \phi_j)\Delta\phi$$

where $D_{aa}$ in Equation (19) is the convolved projected density and in polar coordinates and is given by
$$D_{aa}(r_\alpha, \phi_\alpha) = \int D_{aa}(r', \phi_\alpha) k (r_\alpha - r')dr \quad (20)$$
Here $k(r_\alpha - r')$ is the profile convolution kernel well known in the art. Thus we may write from Equations (18), (19) and (20)

$$(\rho_{aa} \quad \rho_{b\beta})_\tau = \sum_j \sum_{j'} \int\int\{\int D_{aa}(r', \phi_j, t) \cdot \quad (21)$$
$$D_{b\beta}(r'', \phi_{j'}, t-\tau)dt\}k(r_\alpha - r')k(r_\beta - r'')dr'dr''$$

where $D_{a\beta}$ and $D_{b\beta}$ are a function of polar coordinates. Equation (19) provides the advantage of retaining the option of performing the pair wise cross correlation operation $D_{a\alpha} \quad D_{b\beta}$ ray by ray at a speed slow enough to be compatable with more practical, and less expensive hardware than required by Case 1 of Method 2.

The above equations were derived for transmission x-ray beams to obtain net longitudinal flow down a pipe. Several general observations may be made to extend this theory. First, the cross correlation process also yields velocity components perpendicular to the axis of the pipe. This information may be value by itself. Second, the above equations may be modified to make use of data obtained from fluorescence detectors. This is possibly because the associated collimators define paths which are analogous to the transmitted x-ray beams. It is well known in the art of reconstruction tomography that both emission (fluorescence in this case) and transmission x-ray data may be reconstructed using very similar mathematical algorithms.

Further to the previously set forth background information regarding fluorescence, one of the foremost unexploited potentials of radiation reconstruction tomography is the utilization of information contained in the photon energy spectrum of the incident and transmitted beams. This information is used to obtain not only accurate cross-sectional reconstructions of density distributions or structures, but also the distribution of selected chemical elements or materials within the portion of the region or object under study.

Fluorescence Method

The possibilities for obtaining element selective information from a transmitted x-ray beam can be represented by the following equation:

$$I_{sp} = \sum_{e=1}^{E} I_{ospe}W_{pe}\Delta_e V\exp[=\sum_{j=1}^{J}L_{pj}\sum_{k=1}^{K}C_{kj}U_{ke} \quad (22)$$

in which $I_{sp}$ represents the responses of a particular detector p to source s. Here $I_{ospe}$ is the intensity of radiation at each photon energy range e incident on the body. $W_{pe}$ is the efficiency of the detector, $L_{pj}$ is the length of the $p^{th}$ ray in the $j^{th}$ picture volume cell (voxel), $C_{kj}$ is the concentration of the $k^{th}$ element in voxel j, $u_{ke}$ is the photon energy dependent, linear attenuation coefficient of the $k^{th}$ element. $\Delta_e V$ is the width of the $e^{th}$ energy interval. The parameters s,p,e,j and k correspond to source identity, ray path label, photon energy increment, pixel number, and chemical element atomic number, respectively. Equation (22) can be used as the starting point for either material selective projection imaging or material selective reconstruction. Selective projection will be treated first since selective reconstructions can be obtained from such projections by a variety of methods.

For projection imaging, Equation (22) may be written $$I_{sp} = \sum_{e=1}^{E} I_{ospe}W_{pe}\Delta_e V\exp[=\sum_{k=1}^{K}D_{pk}U_{ke}] \quad (23)$$
$$s = 1, \ldots S; p = 1, \ldots P$$
where $\sum_j L_{pj}C_{kj} = D_{pk}, 1 \leq j \leq J \quad (24)$ Selective material imaging is possible if Equation (23) may be solved for the projection concentration $D_{pk}$. Equation (23) may be solved by nonlinear numerical methods or may be written as two sets of linear equations:

$$I_{sp} = \sum_e A_{spe} f_{pe}, S = 1 \ldots S, 1 \leq e \leq E \quad (25)$$

$$\ln F_{pe} = -\sum_k U_{ke} D_{pk} e = 1, \ldots E, 1 \leq k \leq K \quad (26)$$

where $A_{spe} = \sum_e I_{ospe} W_{pe} \Delta e V$ (27)

If $I_{sp}$ is known from the measurement process and $A_{spe}$ is known from calibration procedures, then $f_{pe}$ may be found by solving the set of simultaneous equations by least square or other numerical methods. Note that $u_{ke}$ are known functions obtainable from handbooks and thus the solutions $f_{pe}$ may be used with Equations (27) to solve for $D_{pk}$ for each p. For solutions to exist $S > E$, $R \leq E$ and rank $(U_{ke}) \leq K$ should hold. Matrix $A_{spe}$ is found by spectral measurement or by calibration using pure materials. Here $R = \text{rank}(A_{spe})$.

Images of compounds and complex substances may be formed by proper combination of their pure elemental constituents. Suppose that some substant or material m is composed of fraction $N_{mk}$ of element k. Then Furthermore, the total attenuation $Z_m$ along path p due to substance m is $$\sum_{k=1}^{K} N_{mk} = 1, m = 1,2,\ldots M \quad (28)$$

where $B_{pm}$ is defined to be the area concentration of substance m.

On comparison with Equation (27) $D_{pk}$ may be written $$z_{me} = \sum_k B_{pm} N_{mk} u_{ke}$$

If rank $(B_{pm}) \leq M$ then $B_{pm}$ can be expressed in terms of $D_{pk}$ by $B_{pm} = h_{km} D_{pk}$. Also, by substitution equation (26) becomes $1_n f_{pe}$ $$D_{pk} = \sum_m B_{pm} N_{mk}.$$

where $$pe = \sum_m B_{pm} X_{me}$$

Thus materials rather than elements might be determined directly from transmission measurements.

$$X_{me} = \sum_k u_{ke} N_{mk}.$$

Material Selective Cross-Section Reconstruction Imaging

Chemical element cross section reconstruction (reconstruction tomography) is possible by illuminating the object space from a multiplicity of radiation source positions. The set of Equation (24) may then be solved for the concentration of element k for each set of projection images $D_{pk}$ since $L_{pj}$ is given by the geometry of the source and detector configuration.

In a like manner material selective cross section reconstruction is possible if Equation (22) is modified to include the case of general materials. This is achieved by noting that from the previous expression for $x_{me}$, $u_{ke}$ can be determined. Thus, $$u_{ke} = \sum_m F_{km} x_{me}.$$

Equation (22) can then be written as two equations, namely, Equation (25) and 1n $$f_{pe} = -\sum_m L_{pj} C_{mj} C'_{mj} x_{me}.$$

Note $$C_{mj} = \sum_k C_{kj} F_{km}.$$

An expression for $B_{pm}$ may be found as $$B_{pm} = \sum_j L_{pj} C_{mj}.$$

Thus, the solutions $B_{pm}$ form a set of equations which may be solved for the volume material concentration $C'_{mj}$.

It should be noted that the above theory makes no guarantee that the corresponding equations are well conditioned (i.e. that they have stable and reasonable accurate solutions when using data containing uncertainty and noise). Unfortunately, in some energy intervals the photon energy dependent attenuation coefficient $u_{ke}$ for each chemical element k present may be nearly identical if these elements have nearly equal atomic numbers. Thus transmission data with high signal to noise ratios are required to distinguish chemical elements of nearly equal atomic numbers. The situation is improved for mixtures of elements with widely spaced atomic numbers. Another practical consideration is the question of the maximum number of chemical elements which may be detected independently. In many cases this number is essentially only two because, in some energy intervals, all elements interact with x-rays by two main independent physical mechanisms: photoelectric absorption and Compton scattering. (Above about 1 million electron volts other energy dependent mechanisms such as pair production occur). Thus the most noise free projection and reconstructed images may be obtained by imaging both the photoelectric absorption and Compton scattering interaction density distributions. Nevertheless, such two-component images may often be very useful because they give a measure of the average fraction of high atomic elements (which attenuate mainly by photoelectric absorption) and low atomic number elements (which attenuate proportionally higher by photoelectric absorption than do higher atomic number elements). Such distinctions may be useful in measuring moisture content (water is comprised of low atomic number elements) in medium or high atomic number materials (such as ores) or in determining the amount of ash (contains silicon and calcium) in coal (mainly carbon and hydrogen and oxygen).

Under some circumstances more than two elements may be easily distinguished. This is possible when the sharp photoelectric absorption band edges of the elements present are located within the photon energy range of the detectors used (note: a band edge is a sharp discontinuity of a factor of 3 or more in energy-dependent, absorption coefficient at a series of energies, corresponding to the electronic orbit configuration of each element, which are characteristic for that element). Such sharp features remove the ill conditioning of the corresponding equation (i.e. tend to make each measurement more mathematically orthogonal in terms of vector space representations). For low atomic number elements, these bands occur at such low photon energies that attenuation by all mechanisms makes their use difficult. However, the medium and high atomic number elements may be selectively imaged by use of their band edges. For example, the detection and imaging of iodine has been reported by this inventor and other researchers.

Figure 1:
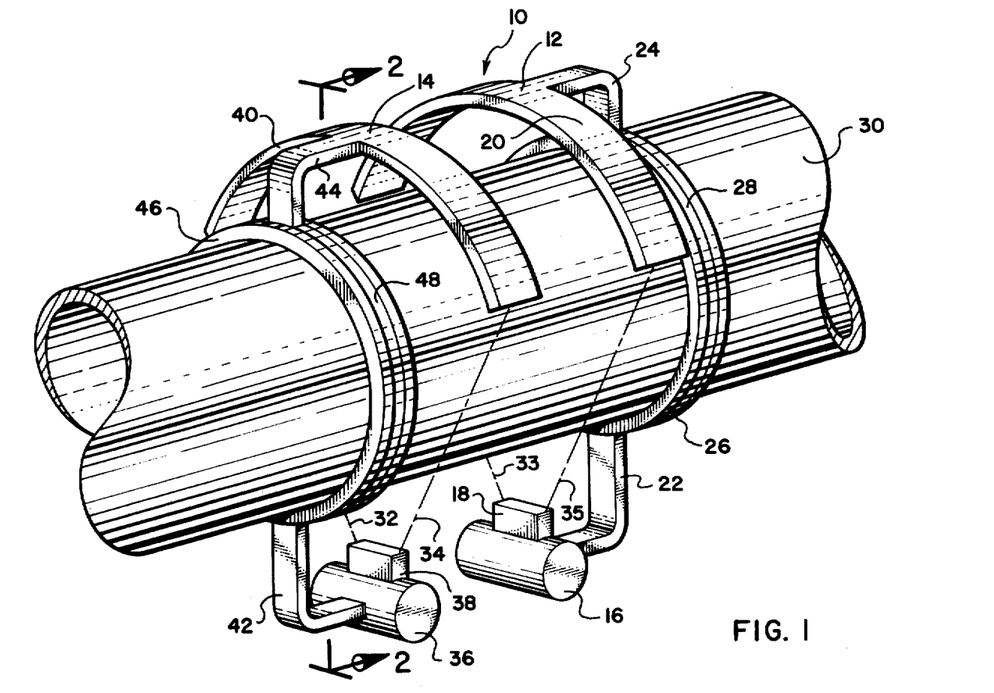
FIG. 1 is a perspective view of a first preferred embodiment of the mass flowmeter of this invention.
Figure 2:
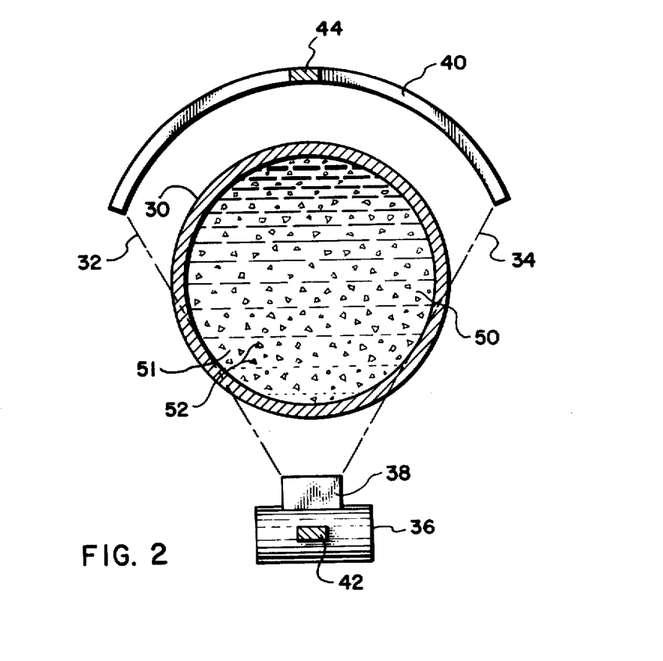
FIG. 2 is a cross section taken along lines 2—2 of FIG. 1.

The Embodiment of FIGS. 1 and 2

Referring now more particularly to FIGS. 1 and 2, a first preferred embodiment of the mass flow meter of this invention is shown generally at 10 and includes meters 12 and 14.

Meters 12 and 14 consist of radiation sources 16 and 36 cooperating with detectors 20 and 40, respectively. Radiation sources 16 and 36 are conventional radiation sources such as, for example where applicable, gamma, x-ray, ultraviolet, visible light, and infrared radiation of the electromagnetic spectrum and ultrasound radiation and include collimators 18 and 38, respectively. Radiation source 16 is mounted on an arm 22 while detector 20 is mounted on an arm 24 so as to be diametrically opposed to radiation source 16. Advantageously, each of arms 22 and 24 are mounted to a rotatable ring 28 cooperating in a flange 26. Ring 28 maintains each of radiation source 16 and detector 20 in a diametrically opposed relationship. Rotation of meter 12 provides a more accurate determination of the characteristics of material in conduit 30 by accommodating measurement across conduit 30 from a plurality of locations as will be set forth more fully hereinafter.

The second meter 14 includes radiation source 36 mounted on an arm 42 and detector 40 mounted on an arm 44, each of arms 42 and 44 being attached to a rotatable ring 48. Rotatable ring 48 is rotatably mounted to conduit 30 by a circular flange 46.

It should be particularly noted that meters 12 and 14 are shown mounted to a conduit 30. However, the various embodiments of this invention are readily adaptable to any suitable system including, but not limited to, vessels, pressure piping, reactors and the like. Accordingly, the foregoing terms are to be considered in all respects as interchangeable wherever appropriate.

Radiation source 16 emits a span of radiation indicated schematically by rays 33 and 35 between the limits of travel indicated thereby in a plane perpendicular to the axis of conduit 30. Rays 33 and 35 are detected by detector 20. Correspondingly, rays 32 and 34 represent a span of radiation emitted by radiation source 36 and are detected by detector 40. The detected radiation is subsequently compared as will be set forth more fully hereinafter to provide an indication of the characteristics of the multiple-phase system in conduit 30.

Conduit 30 is filled with a two-phase system 50 (FIG. 2) shown herein as a fluid 51 having a particulate matter 52 suspended therein. Advantageously, fluid 51 may be any suitable fluid such as a gas or liquid and the particulate matter 52 may be particles of a solid such as coal.

The apparatus illustrated in FIGS. 1 and 2 illustrates a single radiation source and detector combination for each of the two meters 12 and 14 on conduit 30. Clearly, however, multiple radiation source positions and corresponding detector positions may be provided as set forth hereinbefore with regard to Method 2 with the various source positions residing in each of the two, mutually parallel and perpendicular (to the system) scanning planes.

Figure 10:
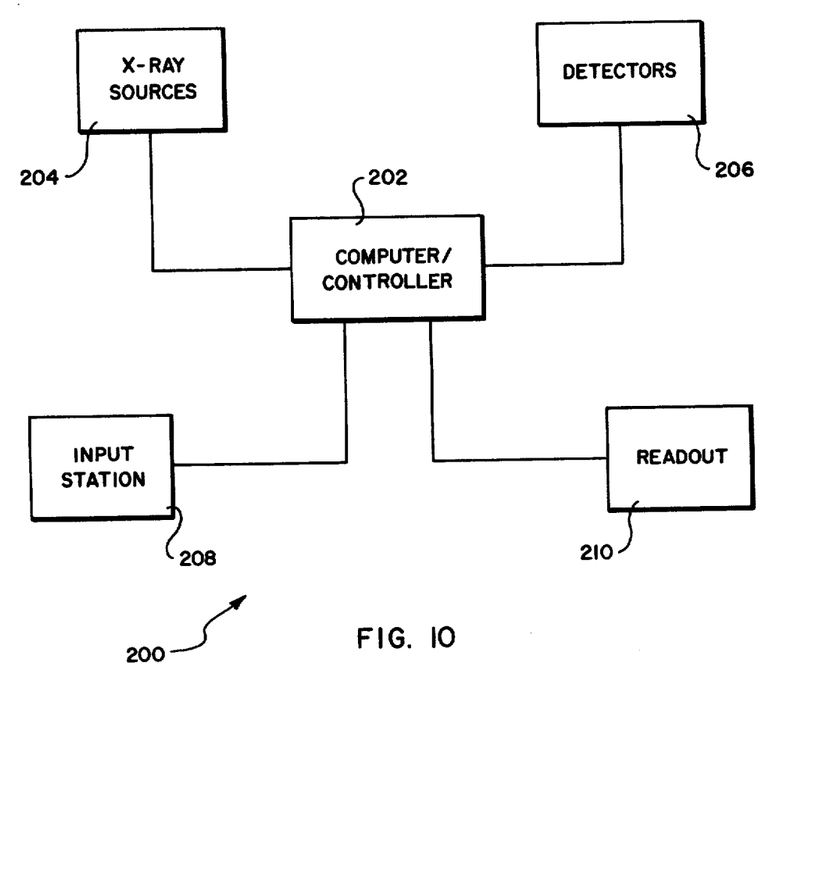
FIG. 10 is a schematic flow diagram for the control of the cross correlation apparatus and other components of this invention.

However, if desired, each of meters 12 and 14, may be suitably rotated about the axis of conduit 30 thereby providing a different source position for the radiation. For example, with particular reference to FIG. 10, computer/controller 202 of control apparatus 200 may be selectively instructed through input station 208 to provide the desired orientation of meters 12 and 14 relative to contuit 30. This is done by rotating rings 28 and 48, respectively, to accommodate x-ray source 204 (radiation sources 16 and 36) emitting radiation toward detectors 206 (detectors 20 and 40, respectively) at predetermined locations around the axis of conduit 30. The data provided thereby is analyzed by computer/controller 202 to provide the predetermined signal output to readout 210.

Figure 3:
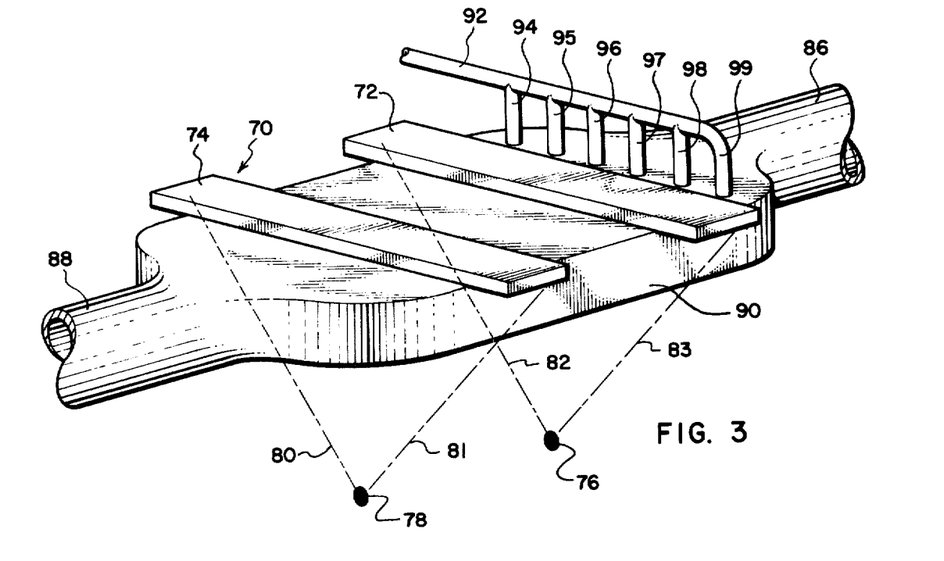
FIG. 3 is a perspective view of a first preferred embodiment of the mass flowmeter of this invention suitable for use in measuring the mass flow rate of a system into which a known phase can be injected.

The Embodiment of FIGS. 3 and 4

Referring now more particularly to FIGS. 3 and 4, the second preferred embodiment of the mass flow meter of this invention is shown generally at 70 and includes at least two radiation sources illustrated schematically at 76 and 78. Corresponding detectors 72 and 74, respectively, are provided. Mass flow meter 70 is mounted over a rectangular plenum chamber 90 interposed between an inlet conduit 86 and an outlet conduit 88. Radiation source 76 emits radiation illustrated herein as rays 82 and 83, which are emitted in a plane perpendicular to the axis of conduits 86 and 88 and detected by detector 72. Correspondingly, radiation source 78 emits rays 80 and 81 which are, in turn, detected by detector 74.

The illustrated embodiment of FIGS. 3 and 4 provides a specific geometry for the simplification of equations for the measurement of mass flow rates. An auxiliar tube 92 for injection of the carrier fluid (such as air or water for coal slurrys) is provided as an optional technique for producing known or detectable phase fluctuations or particulate concentrations for a system in the plenum 90. Cross-correlation signals are thereby enhanced in the event natural fluctuations in the two-phase system 50 (FIG. 2) are insufficient. Auxiliary tube 92 is configurated as a common header having a plurality of injection tubes 94–99 arrayed perpendicularly to the axis of conduits, 86 and 88 and plenum 90 thereby assuring a uniform injection of the appropriate discontinuities or fluctuations in the system.

The Embodiment of FIGS. 6–9

Referring now to the apparatus illustrated in FIGS. 6–9, the multiple-phase flow meter and materials analysis apparatus of this invention is shown generally at 110 and includes an outer, radiation source ring 118, a radiation transmission detector ring 114, a fluorescence detector ring 120, upper and lower collimator rings 116 and 122 for the foregoing radiation transmission detectors 114 and fluorescence detectors 120, respectively. The apparatus of this invention is configurated as concentric, annular rings about a cylindrical conduit or vessel 112.

Figure 7:
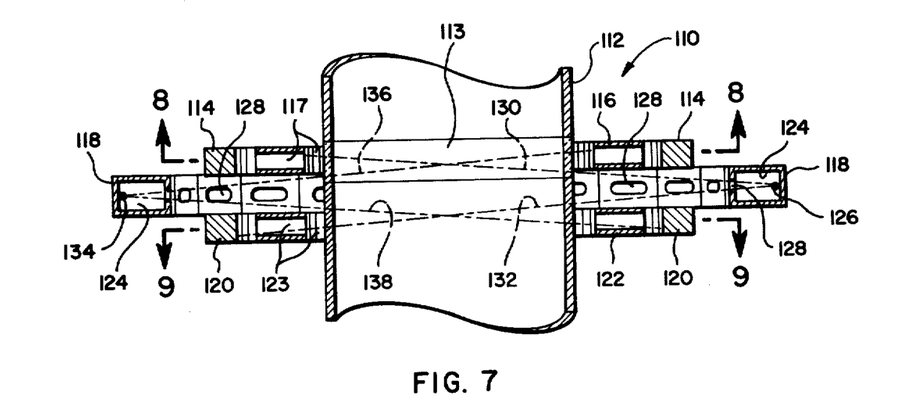
FIG. 7 is a cross section taken along line 7—7 of FIG. 6 and showing a multiple radiation source and multiple collimater and detector apparatus for radiation transmission detection and fluorescence detection.

With particular reference to FIG. 7, radiation source ring 118 includes a plurality of radiation sources and indicated schematically at 126 and 134, each of which are configurated to selectively emit radiation through conduit 112. In particular, radiation source 126 is enclosed within a chamber 124 having a filter aperture 128 in a side-wall thereof. Radiation source 126 emits rays 130 and 132 therethrough. Rays 130 and 132 pass between the adjacent collimator rings 116 and 122 and detector riings 114 and 120. After passing through conduit 112, rays 130 and 132 are either directed or deflected by the opposing collimators 117 and 123 as will be set forth more fully hereinafter with respect to the discussion of FIGS. 8 and 9.

Similarly, radiation source 134 is enclosed within a chamber 124 and emits rays 136 and 138. It should be noted that radiation source ring 118 contains a plurality of chambers, each containing a radiation source similar to radiation sources 126 and 134. Each of the chambers includes the filter aperture 128 therein which is configurated to control the maximum angle at which rays are emitted from the respective radiation source.

Filter apertures 128 can also be fitted with a filter 128 as represented thereby, the filter combining with controlled voltage to the radiation sources 126 and 134 to obtain a selective distribution of radiation therefrom. Accordingly, filters for filter apertures 128 may be suitably preselected to accommodate the appropriate radiation distribution through and into vessel 112.

Although only one analysis apparatus 110 is shown in FIG. 7, it is to be clearly understood that a second, similar apparatus may be emplaced about vessel 112 at a spaced location from analysis apparatus 110. In this manner, sufficient data may be obtained to provide the necessary data input to computer/controller 202 (FIG. 10) as set forth hereinbefore with respect to discussion relating to Equations 1-28, as appropriate.

Figure 8:
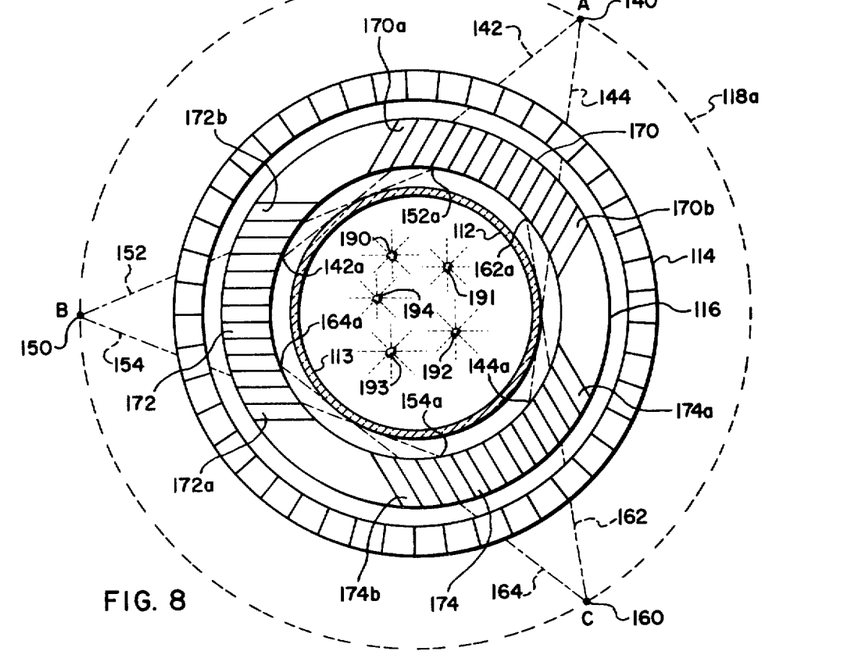
FIG. 8 is a cross section taken along line 8—8 of FIG. 7.

Referring now more particular to FIG. 8, the fluorescence stimulation and detection apparatus of this invention is shown herein with particular emphasis being placed on the orientation of the collimators in collimator ring 116. For purposes of this discussion, three radiation sources (sources 140, 150 and 160) are shown in phantom line as they would be seen in combination with the radiation source ring 118a. Each of the sources 140, 150 and 160 are also indicated as electromagnetic radiation sources A, B and C, respectively. Sources 140, 150 and 160 are spaced at 120° around radiation source ring 118a.

Fluorescence detector ring 114 and collimator ring 116 are coplaner in addition to being coplaner with a transparent section 113 in vessel 112 and all of which are oriented in a plane perpendicular to the axis of vessel 112.

Collimator ring 116 is specifically configured to block radiation from the opposite source against being detected by the underlying detectors in fluorescence detector ring 114. For example, source 140 emits a span of between rays 142 and 144 which pass underneath the near side of fluorescence detector ring 114 and collimator ring 116. Rays 142-144 penetrate conduit 112 and stike a plurality of particles 190-194 therein causing the same to fluoresce, the fluorescence being detected by the fluorescence detectors in fluorescence detector ring 114. It should be noted that rays 142 strike collimator set 172 at a point indicated by 142a and the orientation of collimator set 172 is such that rays 142 are inhibited from striking the adjacent fluorescence detectors in fluorescence detector ring 114. Correspondingly, ray 144 strikes collimator set 174 at 144a and the orientation of collimator set 174 is such that rays 144 are inhibited from striking the underlying fluorescence detectors in fluorescence detector 114. It should be further noted that the gap between collimator 172a and collimator 174b is configurated as a non-transmitting section of collimator ring 116 to preclude the direct contact of radiation from source 142 on the underlying fluorescence detectors of fluorescence detector ring 114.

Similar features are found for each of rays 152 and 154 emitted by source 150 and rays 162 and 164 emitted by source 160 in conjunction with their corresponding collimator sets 170, 172 and 174. Additionally, the spaces between collimators 170a and 172b as well as 170b and 174a are also configurated as non-transmitting sections for the purposes set forth hereinbefore. In the configurations shown herein the various collimator sets and non-transmitting sections of collimator ring 116 suitably inhibit the impingement of radiation on the fluorescence detectors in fluoresence detector ring 114 to thereby substantially minimize spurious readings by the fluorescence detectors that would otherwise result from direct contact with the radiation.

Fluorescence detectors in fluorescence detector ring 114 are configurated as commercially available detectors and may be coupled with appropriate filters, also commercially available, to improve selectivity and sensitivity of analysis apparatus 110. The detectors are identified as being photon energy discriminating detectors.

The radiation from sources 140, 150 and 160, is any suitable electromagnetic radiation and strike particles 190-194 causing the same to fluoresce according to their well-known fluorescence characteristics. Fluorescence is schematically indicated by the broken lines emanating from each of particles 190-194. The fluorescence is emitted from each of particles 190-194 and is transmitted through transparent section 113 where it is directed by collimator sets 170, 172, and 174 to the respective, underlying fluorescence detectors in fluorescence detector ring 114. The fluorescence thus detected by the respective fluorescence detectors in fluorescence detector ring 114 provides thereby an indication of the elemental composition of particles 190-194.

Advantageously, radiation source ring 118 (FIGS. 6 and 7) includes a plurality of radiation sources arrayed around radiation source ring 118. Accordingly, it is possible to selectively control the emission of x-rays from the various x-ray sources therein. In conjunction, collimator ring 116 can be selectively indexed in combination with the respective x-ray sources so as to provide the necessary collimation for fluorescence detection while inhibiting spurious readings from direct impingement of radiation on the various fluorescence detectors in fluorescence detector ring 114.

It should be particularly noted that collimator ring 116 and the collimator sets 170, 172 and 174 are specifically configurated to the simultaneous functioning of three sources 140, 150 and 160 spaced at 120° intervals around radiation source ring 118. Other multiples of radiation sources may be utilized by suitably reconfigurating the number and orientation of the collimator sets in collimator ring 116. Additionally, radiation source ring 118 and collimator ring 116 could be rotatable about vessel 112 similar to meters 12 and 14 (FIGS. 1 and 2) to provide additional capabilities.

Figure 9:
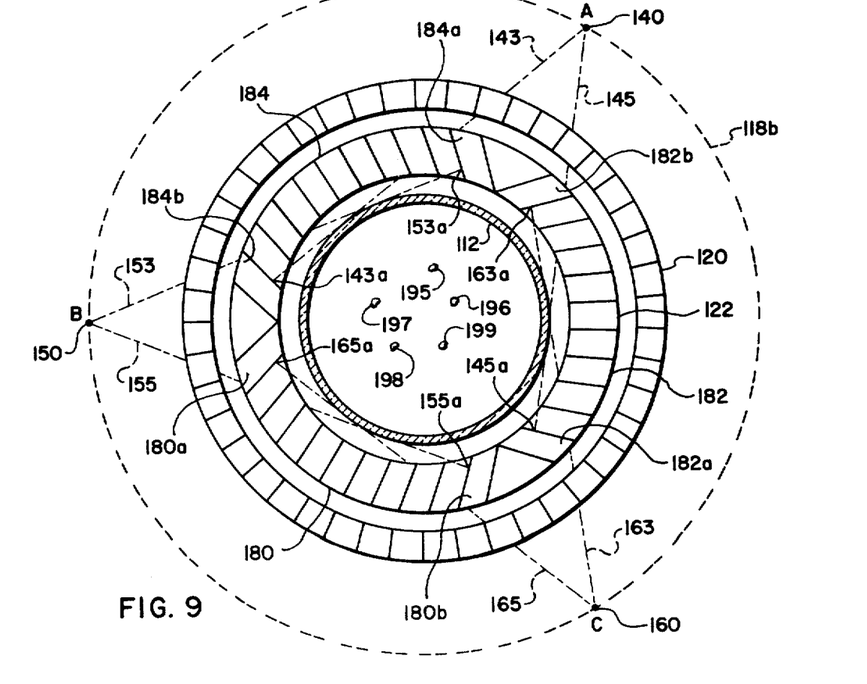
FIG. 9 is a cross section taken along lines 9—9 of FIG. 7.

Referring now more particularly to FIG. 9, the radiation transmission collimator and detector apparatus of this third preferred embodiment of this invention is shown herein and includes transmitted radiation detector ring 120 which is coplaner with collimator ring 122 in a plane perpendicular to the axis of vessel 112. Radiation sources 140, 150 and 160 are shown in phantom lines on a phantom line, radiation source ring 118b (indicating radiation source ring 118, FIGS. 6 and 7). Since transmitted radiation detector ring 120 requires the direct impingement on radiation thereon, each of the collimator sets 180, 182 and 184 are configured to expose the underlying transmitted radiation detectors of transmitted radiation detector ring 120 to radiation emitted from the corresponding radiation source on the opposite side of vessel 112. For example, radiation source 140 emits radiation between rays 143 and 144, which penetrate vessel 112 and are directed by collimator set 182 into the adjacent transmitted radiation detectors of transmitted radiation detector ring 120. Correspondingly, collimator set 182 directs rays 153-155 into the adjacent transmitted radiation detector while collimator set 184 directs rays 163-165 into the adjacent transmitted radiation detectors thereunder. Radiation outside the appropriate collimator sets is blocked and inhibited from striking an adjacent transmitted radiation detector. For example, rays 143 and 145 pass underneath the adjacent portions of transmitted radiation detector ring 120 and collimator ring 122 and, at the outermost limits, strike collimator sets 184 at 143a and collimator set 182 at 145a, respectively. Similar features are found for rays 153 and 155 striking collimator sets 184 at 153a and collimator set 180 at 155a, respectively. Additionally, rays 163 and 165 from radiation source 160 also strike collimator sets 182 at 163a and 180 at 165a, respectively. In this manner, only those rays transmitted directly through vessel 112 are permitted to be detected by the appropriate transmitted radiation detectors in transmitted radiation detector ring 120.

It should also be noted that at least one collimator set similar to collimator sets 180, 182, and 184 may be incorporated with the apparatus of meters 12 and 14 (FIGS. 1 and 2) and provide substantially the same function therein.

In operation, each of radiation sources 140, 150 and 160 may be initiated simultaneously, the respective radiation therefrom striking or bypassing particles 195-199 in vessel 112 so that the radiation detected by the transmitted radiation detectors in transmitted radiation detector ring 120 provide an indication of the particulate distribution in conduit 112.

With particular reference again to FIG. 10, the control apparatus 200 may be selectively instructed through input station 208 to provide the desired orientation of radiation sources 140, 150, and 160 (FIGS. 8 and 9) and 126 and 134 (FIG. 7) in combination with collimators 170, 172 and 174 (FIG. 8) and 180, 182, and 184 (FIG. 9). The information received by the fluorescence detectors of fluorescence detector ring 114 (FIGS. 7 and 8) and detectors of transmitted radiation detector ring 120 (FIGS. 7 and 9) is suitably correlated by computer/controller 202 to provide the preselected instructions for readout 210. For example, the equipment of control apparatus 200 may be selectively assembled and controlled/instructed to provide readout, inter alia, relating to density distribution, flow velocity, elemental analysis and distribution, mass flow rate, and the like, as set forth through out this disclosure.

Furthermore control apparatus 200 and, more particularly, computer controller 202 in its control of x-ray sources 204 can be suitably instructed by conventional techniques to preselect a suitable filter 128 (FIG. 7) for the various radiation sources 126 and 134 (FIG. 7); 100 (FIG. 5); 78 (FIGS. 3 and 4); or 16 and 36 (FIGS. 1 and 2) and thereby provide the desired wavelength spectral distribution required for improved data to reconstruct the density, velocity and mass density along with the averages at each cross section. Filter selection is coupled with voltage regulation to the various radiation sources to achieve this desirable result.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes that come within the meaning and range of equivalency of the claims are to be embraced within their scope.

What is claimed and desired to be secured by a U.S. Letters Patent is:

1. A non-invasive meter apparatus comprising:
    a first radiation source and first radiation detector demountably attachable to a vessel at a first location;
    a second radiation source and a second radiation detector demountably attachable to said vessel at a second location;
    computing means for comparing radiation signals detected by the first detector with radiation signals received by the second detector; and
    control means for selectively controlling the first and second radiation sources and the first and second detectors.

2. The apparatus defined in claim 1 wherein the first radiation source comprises a plurality of first radiation sources, the first radiation detector comprises a plurality of first radiation detectors, the second radiation source comprises a plurality of second radiation sources and the second radiation detector comprises a plurality of second radiation detectors.

3. The apparatus defined in claim 1 wherein the first detector further includes a first fluorescence detector and the second detector further includes a second fluorescence detector.

4. The apparatus defined in claim 1 wherein the first radiation source and the second radiation source further comprise filter means and voltage control means to thereby obtain a predetermined wavelength spectral distribution from the first and second radiation sources in order to provide improvements in reconstructing density, velocity and mass density at each point in a given cross section of the vessel and the averages over the cross section of the vessel.

5. The apparatus defined in claim 1 wherein the first radiation source and the second radiation source are selected as ultrasound sources.

6. An apparatus for non-invasive detection of system characteristics comprising:
    a first radiation source;
    a first detector for the first radiation source, said first detector further comprising a first fluorescent radiation detector;
    a second radiation source;
    a second detector for the second radiation source, said second detector further comprising a second fluorescent radiation detector;
    mounting means for mounting the first radiation source and the first detector externally of the system with the first radiation source being mounted opposite the first detector at a first position and the mounting means also accommodating mounting the second radiation source and the second detector externally of said system at a second position spaced from the first position with the second radiation source being mounted opposite the second detector; and computation means for comparing a first set of radiation signals transmitted from the first radiation source to the first detector with a second set of radiation signals transmitted from the second radiation source to the second detector.

7. The apparatus defined in claim 6 wherein the first radiation source and the second radiation source are selected having a wavelength between the shorter wavelength ranges of the electromagnetic spectrum at the gamma wavelength range and the longer wavelength ranges of the electromagnetic spectrum at the infrared wavelength range.

8. The apparatus defined in claim 6 wherein the first and second radiation sources each comprise a plurality of radiation sources and the first and second detectors each comprise a plurality of detectors for the respective first and second radiation sources.

9. The apparatus defined in claim 8 wherein the first detectors comprise a first set of collimators, the first set of collimators providing limitation of radiation from each radiation source of the first radiation source to a preselected first detector and the second detectors comprise a second set of collimators, the second set of collimators providing limitation of radiation from each radiation source of the second radiation source to a preselected second detector.

10. The apparatus defined in claim 9 wherein the first set of collimators comprises a first set of radiation collimators for the first radiation detectors and a first set of fluorescent radiation collimators for the first fluorescent radiation detectors and the second set of collimators comprises a second set of radiation collimators for the second radiation detectors and a second set of fluorescent radiation collimators for the second fluorescent radiation detectors.

11. The apparatus defined in claim 10 wherein the mounting means further comprises indexing means for indexing each of the first set of radiation collimators, the first set of fluorescent radiation collimators, the second set of radiation collimators, and the second set of fluorescent radiation collimators in coordination with radiation sources.

12. An apparatus for assaying the elemental composition of a system comprising:

a plurality of electromagnetic radiation sources circumferentially arrayed in a first plane perpendicular to an axis of the system, each electromagnetic radiation source operable to transmit electromagnetic radiation into the system, the electromagnetic radiation causing the elements to fluoresce;

a plurality of fluorescent radiation detectors circumferentially arrayed in a second plane parallel to the first plane for detecting fluorescence emitted by the elements;

collimator means for delimiting the fluorescent radiation detector against spurious readings from the electromagnetic radiation;

switching means for selectively activating preselected electromagnetic radiation sources and fluorescent radiation detectors;

indexing means for selectively rotating the collimator means to inhibit electromagnetic radiation from being directly detected by the fluorescent radiation detectors while allowing fluorescence to be detected by the detectors; and analyzing means for analyzing the detected fluorescence as a function of the elemental composition of the system.

13. The apparatus defined in claim 12 wherein the apparatus further comprises detector means for determining the elemental distribution in a cross section of the system.

14. An apparatus for non-invasive detection of system characteristics comprising:

a first radiation source;

a first detector for the first radiation source;

a second radiation source;

a second detector for the second radiation source;

mounting means for mounting the first radiation source and the first detector externally of the system with the first radiation source being mounted opposite the first detector at a first position and the mounting means also accommodating mounting the second radiation source and the second detector externally of said system at a second position spaced from the first position with the second radiation source being mounted opposite the second detector, the mounting means further comprising a first track externally mountable on the system adjacent the first position to accommodate rotational movement of the first radiation source and first detector about the system and a second track externally mountable on the system adjacent the second position to accommodate rotational movement of the second radiation source and the second detector about the system; and computation means for comparing a first set of radiation signals transmitted from the first radiation source to the first detector with a second set of radiation signals transmitted from the second radiation source to the second detector.

15. The apparatus defined in claim 14 wherein the first track and the second track are separable units to accommodate being independently and adjustably mounted to the system at preselected separation distances.

16. An apparatus for non-invasive detection of system characteristics comprising:

a first radiation source;

a first detector for the first radiation source;

a second radiation source;

a second detector for the second radiation source;

mounting means for mounting the first radiation source and the first detector externally of the system with the first radiation source being mounted opposite the first detector at a first position and the mounting means also accommodating mounting the second radiation source and the second detector externally of said system at a second position spaced from the first position with the second radiation source being mounted opposite the second detector;

injection means for injecting a known phase into the system to provide thereby a known phase fluctuation in the system; and computation means for comparing a first set of radiation signals transmitted from the first radiation source to the first detector with a second set of radiation signals transmitted from the second radiation source to the second detector.

17. A method for measuring mass flow characteristics in a system comprising:
- directing a first radiation through a conduit at a first location to a first detector;
- directing a second radiation through the conduit at a second location to a second detector;
- injecting a control phase into the system thereby providing improvements in detectable phase differences in the system for the first and second radiation; and
- comparing the first radiation detected by the first detector with the second radiation detected by the second detector as a function of the flow characteristics.

18. A method for measuring mass flow characteristics in a system comprising:
- directing a first radiation through a conduit at a first location to a first detector;
- directing a second radiation through the conduit at a second location to a second detector;
- comparing the first radiation detected by the first detector with the second radiation detected by the second detector as a function of the flow characteristics; and
- detecting fluorescence with a fluorescent radiation detector thereby providing an indication of the elemental composition within the system.

19. An apparatus for assaying the elemental composition of a system comprising:
- a first analysis apparatus comprising:
  - at least one electromagnetic radiation source operable to transmit electromagnetic radiation into the system, the electromagnetic radiation causing the elements to fluoresce;
  - at least one fluorescent radiation detector means for detecting fluorescence emitted by the elements; and
  - analyzing means for analyzing the detected fluorescence as a function of the elemental composition of the system;
- a second analysis apparatus spaced from the first analysis apparatus a discrete distance on the system; and
- cross correlation means for cross correlating the detected information of both apparatus.

* * * * *